United States Patent [19]

Flick et al.

[11] Patent Number: 5,516,851

[45] Date of Patent: May 14, 1996

[54] SUPPORTED CATALYSTS

[75] Inventors: Klemens Flick, Herxheim; Peter Polanek, Weinheim; Dietmar Posselt, Ludwigshafen, all of Germany

[73] Assignee: BASF Aktiengesellschaft, Ludwigshafen, Germany

[21] Appl. No.: 341,997

[22] Filed: Nov. 16, 1994

[30] Foreign Application Priority Data

Nov. 16, 1993 [DE] Germany .............. 43 39 138.9

[51] Int. Cl.$^6$ ...................................... C08F 8/42
[52] U.S. Cl. .................. 525/330.2; 525/330.6; 525/370; 525/371; 502/159
[58] Field of Search ............ 502/159; 525/330.2, 525/330.6

[56] References Cited

U.S. PATENT DOCUMENTS 4,762,956 8/1988 Liu et al. ...................... 585/259

FOREIGN PATENT DOCUMENTS 569077 11/1993 European Pat. Off. .

OTHER PUBLICATIONS

*Patent Abst. of Japan*, vol. 010, No. 123 (C–344) May 8, 1986 (English abstract of JP–A 60 248237, Dec. 7, 1985).

Primary Examiner—Bernard Lipman
Attorney, Agent, or Firm—Keil & Weinkauf

[57] ABSTRACT

Supported catalysts, obtainable by
a) dissolving a catalytically active component or its intermediate in a solvent,
b) adding an organic polymer which is capable of binding at least ten times its own weight of water to the solution thus obtained,
c) then mixing the polymer with a catalyst carrier,
d) molding the material thus obtained, drying and calcining, a process for their preparation and their use.

5 Claims, No Drawings

SUPPORTED CATALYSTS

The present invention relates to supported catalysts, a process for their preparation and hydrogenation processes using said catalysts.

The distribution of catalytically active components in supported catalysts plays a decisive role with regard to their activity, selectivity and life. If supported catalysts are prepared, for example, by impregnation of porous catalyst carriers with solutions which contain the catalytically active components or their intermediates, or by coprecipitation of the active components and of the carrier, the active components are uniformly distributed over the entire catalyst or a coat containing active components is formed. Since, as a rule, micropores having a diameter of <20 nm form the main proportion of the internal surface area of a catalyst, the active components are for the most part present in these micropores. However, the micropores are more difficult for the reactants to reach than are mesopores and macropores (from 20 to 100 nm and >100 nm diameter, respectively). Particularly in the case of diffusion-controlled reactions, this leads to a low activity and selectivity since undesirable secondary reactions take place preferentially in the micropores. In the case of catalytic reactions with bulky molecules, the conversion possible owing to the catalytically effective amount of active components in the catalyst or the activity decreases, since these molecules cannot penetrate into the micropores.

JP-A 84/104 678 relates to a process for the preparation of supported catalysts, a crosslinked polyacrylic acid, water, kieselguhr as a carrier and vanadium oxide as an active component being mixed, the mixture being extruded, the extrudate being cut into rings and the rings being calcined at 550° C. The catalyst thus obtained possesses good processing properties during extrusion.

It is an object of the present invention to provide supported catalysts whose active components are predominantly present in mesopores and macropores.

We have found that this object is achieved by supported catalysts which are obtainable by a) dissolving a catalytically active component or its intermediate in a solvent, b) adding an organic polymer which is capable of binding at least ten times its own weight of water to the solution thus obtained, c) then mixing the polymer with a catalyst carrier, d) molding the material thus obtained, drying and calcining.

We have also found a process for the preparation of these supported catalysts and their use.

The novel catalysts are prepared by the process steps described below.

Process step a)

The catalytically active components or their intermediates, which are not converted into active components until further processing or activation steps, are dissolved in a solvent. The solvents are preferably polar, water-miscible solvents, such as alcohols, ethers and amines. Particularly suitable alcohols are $C_1$–$C_4$-alcohols, such as methanol, ethanol, isopropanol and n-butanol. An example of a suitable ether is tetrahydrofuran. Amines to be used according to the invention are ammonia, monoamines, such as dimethylamine, methylamine, trimethylamine, ethylamine, propylamine and butylamine. However, water or an ammonia/water mixture is particularly preferred.

The catalytically active components are in general water-soluble salts of transition metals, such as palladium nitrate, palladium acetate, ammonium hexachloropalladate(IV), ammonium tetrachloropalladate(II), dichlorodiamminepalladium(II), potassium hexachloropalladate(IV), potassium tetrachloropalladate(II), sodium tetrachloropalladate(II), palladium acetylacetonate, palladium chloride(II), palladium sulfate(II), dichlorotetraamminepalladium(II), tetraamminepalladium nitrate, platinum chloride, ammonium hexabromoplatinate, ammonium hexachloroplatinate(IV), ammonium tetrachloroplatinate(II), barium tetracyanoplatinate(II), hexachloroplatinic(IV) acid, potassium hexabromoplatinate(IV), potassium hexachloroplatinate(IV), potassium tetrachloroplatinate(II), potassium tetracyanoplatinate(II), sodium hexachloroplatinate(IV), diammineplatinum(II) chloride, tetraammine platinum(II) chloride and tetraammineplatinum(II) nitrate; silver nitrate, acetate, sulfate, cyanide, carbonate and thiocyanate; copper nitrate, acetate, sulfate and chloride; zinc nitrate, acetate, sulfate, chloride and carbonate; Fe(II) chloride, Fe(III) chloride, iron nitrate and iron sulfate; chromium chloride and sulfate, potassium dichromate and potassium chromate; nickel nitrate, acetate, sulfate and chloride; manganese sulfate and chloride, potassium permanganate; cobalt nitrate, acetate, sulfate and chloride; ammonium hexachlororhodate(III) and sodium hexachlororhodate(III); rhodium(III) chloride, rhodium acetate, rhodium(III) nitrate and rhodium(III) sulfate; ruthenium nitrate, acetate and nitrosylnitrate; rhenium(VII) oxide, ammonium perrhenate, sodium perrhenate, potassium perrhenate and perrhenic acid; osmium chloride, ammonium hexachloroosmate, osmium(VIII) oxide; potassium hexachloroosmate(IV) and potassium osmate(VI).

These compounds are commercially available. Sols of the metals palladium, platinum, silver and copper, as obtainable, for example, according to Angew. Chem. 103 (1991), 852 or in some cases commercially available, are also suitable.

Preferred compounds are the salts of platinum, silver, nickel, copper and palladium, particularly preferably palladium acetate, nitrate and chloride.

If, in addition to the actual active components, the supported catalysts are furthermore intended to contain promoters or moderators which may influence the catalytic activity or selectivity, it is advantageous to add these, directly or likewise in the form of their intermediates, to the solution of the transition metal salts or sols. Specific examples of promoters or their intermediates are:

nitrates, acetates, chlorides, sulfates and hydroxides of the alkali metals lithium, sodium, potassium and cesium and of the alkaline earth metals magnesium, calcium, barium and strontium, as well as sulfates of the alkali metals and of magnesium and calcium, and finally carbonates of the alkali metals and magnesium carbonate. Phosphates, such as sodium phosphate, arsenates, such as ammonium, sodium and potassium arsenate, lead compounds, such as lead acetate, lead chloride and lead nitrate, bismuth compounds, such as bismuth nitrate and bismuth oxychloride, tin compounds, such as tin chloride, or alkali metal stannates, and antimony compounds, such as ammonium, sodium and potassium antimonate.

The concentration of the transition metal salt solutions or sol solutions depends on the one hand on the solubility of the corresponding compounds. It should be, as a rule, at least 0.1 g/l and may be up to saturation of the solution. As a rule, the solutions contain from 0.01 to 5 % by weight of transition metal ions. Furthermore, the amount of the active component depends on its desired concentration in the novel supported catalyst. The solutions are generally prepared at room temperature.

Process step b)

An organic polymer is added to the solutions, described above, of the active components or their intermediates, and either the solution may be added to the polymer or the polymer to the solution.

The organic polymer is capable of binding at least ten times its own weight of water. Such compounds are referred to as hydrogels (cf. B. D. Rathmer et al. in Hydrogels for Medical and related Applications, ACS Symposium Series No. 31 (1976)). These are crosslinked polymeric compounds, where the crosslinking may be effected by ionic interactions or hydrogen bridge bonds and by chemical crosslinking. For example, graft copolymers of starch and acrylonitrile (for example, G. F. Fanta et al. in Starch 34 (1982) 95), starch and acrylic acid (EP-A 83 022), polysaccharides and acrylic acid (DE-A 41 05 000), copolymers of polyvinyl alcohol and sodium acrylates (U.S. Pat. No. 4 155 893), copolymers of acrylamide and acrylic acid (EP-A 72 214), crosslinked polyethylene oxide (U.S. Pat No. 3 264 202), crosslinked polyacrylamide (U.S. Pat No. 3 669 103), crosslinked poly-N-vinylpyrrolidone (U.S. Pat No. 3 669 103), crosslinked polyvinyl alcohols (Walter et al., Biomaterials 9 (1988) 150), crosslinked carboxycellulose fibers (U.S. Pat No. 3 826 711), hydrolysis products of polyvinyl acetate/acrylic acid copolymers (GB 20 30 990) and hydrolysis products of polyacrylonitrile (U.S. Pat. No. 4 366 206).

Crosslinked polymers of acrylic acid, or acrylic acid and acrylamide and of acrylamide are preferred. Partially neutralized sodium polyacrylates which are slightly crosslinked are particularly preferred. Examples of suitable chemical crosslinking agents are diols, such as ethylene glycol, polyethylene glycol and polyols, diamines and dienes in amounts of from 0.1 to 5 % by weight, based on the polymer. Such polymers can bind up to 1000 times their own weight of water. They are usually prepared by free radical polymerization in aqueous solution and are commercially available as thickeners or superabsorbers (F. L. Buchholz, Preparation and Structure of Polyacrylates in Absorbent Polymer Technology, Studies in Polymer Science 8, Elzevier, Amsterdam 1990, page 23).

In general, the solution of the active component is added to the polymer in an amount such that the latter can completely absorb said solution. The polymer swells as a result. This process is in general complete in 60 minutes. The swelling of the polymer is usually carried out at room temperature. During the swelling of the polyacrylates, the pH should be at least 6, since otherwise insufficient solution is absorbed.

Process step c)

The swollen polymer is mixed with a catalyst carrier in powder form, the order in which the components are added to one another being unimportant.

Suitable carriers are compounds which are inert under the reaction conditions of the reaction to be catalyzed, preferably aluminas, silica, kieselguhr, silica gel, clay minerals, eg. montmorillonite, silicates, zeolites as a mixture with alumina, zirconium oxides and titanium oxides and mixtures of these compounds with one another, among which alumina and silica are particularly preferred.

Oxides of Mg, Ca, Sr, Ba, sulfates of Ca, Ba, Sr and Pb, carbonates of Mg, Ca, Sr, Ba, Ni, Co, Mn, Fe and Cu, sulfides of Mo, W, Co, Ni, Fe, Pb, Ag, Cr, Cu, Cd, Sn and Zn, carbides of B, Si and W and nitrides of B and Si may also be used.

The amount of carrier is in general from 10 to 1000, preferably from 20 to 200, times the amount of the unswelled polymer.

Conventional peptizing agents may be added to the solution to improve the mechanical stability of the moldings obtained, for example ammonia for alumina carriers and sodium hydroxide solution for silica. The amount is, as a rule, from 0.1 to 5 % by weight, based on the carrier.

The components are mixed, and kneaders or mix-mullers may be used for this purpose.

Process step d)

The further processing measures are known per se to a person skilled in the art. The material obtained according to process step c) is molded, for example by extrusion in an extruder, to give extrudates having the desired dimensions. The moldings thus obtained are dried, as a rule temperatures of 100°–150° C. over 2 to 24 hours being used for this purpose.

The moldings are then calcined in general for from 2 to 24 hours at from 300° to 800° C., preferably from 300° to 550° C., the polymers being removed from the carrier matrix and the thermally unstable salts of the active components being converted into the oxides, mixed oxides or halides. Depending on the active component, this may be followed by an activation step, the catalytically active component being formed only at this stage. In the case of hydrogenation catalysts, this is effected, for example, by treatment with hydrogen at from 80° to 400° C. under, in general, atmospheric pressure in a stream of hydrogen.

The drying step may also be omitted, but it has been found that it is advantageous for gentle removal of the solvent.

The supported catalysts thus obtained may furthermore be applied in a conventional manner to nonporous carriers comprising, for example, steatite or to glass rings, quartz rings or highly sintered alumina rings. For this purpose, milled supported catalyst particles and a granulating liquid are generally added to the nonporous carriers. This liquid may be an aluminum nitrate solution, aluminum acetate solution or aluminum sodium hydroxide solution, each of which, after drying and calcination of the coated nonporous carriers, forms solid bridges between the nonporous carriers and the catalyst particles.

The novel supported catalysts are highly porous and have a low bulk density. Electron micrographs show clearly that the predominant part, as a rule more than 80 %, of the active components is present in the macropores. Determination of the proportion of the active component which is present in the macropores is possible only by evaluating a plurality of representative sections through the catalyst extrudate, in scanning electron microscopy the heavy elements being rendered visible with the aid of the back-scattered electrons.

In the novel catalysts, the reactants can readily reach the reactive centers and the reaction products can easily be removed. By arranging the active components in the macropores, it is possible to prepare catalysts which, while having the same activity as conventional catalysts, require only a fraction of the amount of active component.

The novel supported catalysts are particularly suitable for hydrogenations, especially those in the liquid phase. Examples of these are (the particular preferred active components are shown in parentheses):

the selective hydrogenation of polyunsaturated hydrocarbons in $C_2$–$C_{10}$-hydrocarbon streams which are formed in catalytic or thermal crack or pyrolysis processes in refineries or steam crackers, in particular the hydrogenation of acetylene in a $C_2$ stream (Pd, Pt, Cu), the hydrogenation of methylacetylene and propanediene in a $C_3$ stream (Pd, Pt, Cu, Ag), the hydrogenation of butadiene, butyne and vinylacetylene in a $C_4$ stream (Pd, Pt, Cu), the hydrogenation of cyclopentadiene, pentadiene and isoprene in a $C_5$ stream (Pd, Pt, Cu, Ni) and the hydrogenation of dienes and styrene in a $C_5$–$C_{10}$ stream (pyrolysis gasoline) (Pd, Pt, Cu, Ni), the refinement, with hydrogenation, of long-chain hydrocarbons from refinery streams, in particular the degradation of oxygen, sulfur, nitrogen and aromatic compounds under hydrogenating conditions in light naphtha, heavy naphtha, gas oils, vacuum gas oils, residues, in particular the refinement, under hydrogenating conditions, of solvent-refined and deparaffinized vacuum gas oils to give technical and medical white oils (Ni, Mo, W, Pt, Pd) and refinement, under hydrogenating conditions, of paraffins (Ni, Mo, W, Pt, Pd) and the hydrogenation of edible fats (hardening of fats) (Ni, Pd, Pt), selective hydrogenations of functional groups in polymers, in particular the hydrogenation of olefinic double bonds in styrene/butadiene copolymers (Ni, Pd, Pt), isomerizations, in particular the skeletal isomerization of n-butane to isobutane (Pd, Pt), dehydrogenations of $C_3$–$C_{15}$-hydrocarbon streams using Pd- or Cr-containing catalysts, in particular the dehydrogenation of isobutene
the dehydrogenation of butane to butenes and butadiene
the dehydrogenation of propane to propene
the dehydrogenation of isopentane to isoprene
the dehydrogenation of $C_6$–$C_{15}$-paraffins, selective oxidations, in particular the selective oxidation of ethylene to ethylene oxide (Ag, Cu) and the selective oxidation of ethylene glycol to glyoxal (Ag, Cu).

In the case of dehydrogenations, the novel supported catalysts have less tendency to coke or longer lives, owing to the faster mass transfer in the macropores and the associated shorter residence time at the surface (cf. A. Wheeler, Adv. Catal. 3 (1951), 17).

EXAMPLES

Example 1

Preparation of a novel supported catalyst (Pd on $Al_2O_3$)

50 ml of water and 3 g of a high molecular weight sodium polyacrylate (90 % of the acid groups neutralized, crosslinked with 0.4 mol % of polyethylene glycol having a molecular weight of 500) which binds 300 times its own weight of water were added to 5.47 g of an aqueous palladium nitrate solution (11% by weight of Pd). After 0.5 hour, the gel-like mass was kneaded with 280 g of alumina (pseudoboehmite, surface area after calcination at 600° C.: 300 m²/g). After the addition of 200 ml of ammonia solution (containing 50 ml of concentrated ammonia), kneading was carried out for 1 hour. The mass was molded at 65 bar in an extruder to give 3.8 mm extrudates, which were dried for 16 hours at 120° C. and calcined for 6 hours at 330° C.

Analytical data of the catalyst:

| Weight per liter | 383 g/l |
|---|---|
| BET surface area | 298 m²/mg |
| Pore volume (DIN 66 132) | 1.17 ml/g |

(determined by mercury porosimetry, J. v. Brakel et al., Powder Technology 29 (1991), 1)

Micropores have a diameter of <20 nm, mesopores of from 20 to 100 nm and macropores of >100 nm.

The novel catalyst has the following analytical data:

Mean diameter of the macropores [nm]: 600

Mean diameter of the micro- and mesopores [nm]: 4

Proportion of macropores [% by volume]: 33

Example 2

Preparation of a comparative catalyst (Pd on $Al_2O_3$)

3 g of a high molecular weight sodium polyacrylate (90 % of the acid groups neutralized, crosslinked with 0.4 % of polyethylene glycol having a molecular weight of 1500) which binds 300 times its own weight of water were mixed with 280 g of pseudoboehmite in a kneader (powder A).

5.47 g of an aqueous palladium nitrate solution (11% by weight of Pd) were dissolved in 150 ml of water. This Pd-containing solution was added to powder A. After the addition of 200 ml of ammonia solution (containing 50 ml of concentrated ammonia), kneading was carried out for 1 hour. The material was extruded to give 3.8 mm extrudates, which were dried for 16 hours at 120° C. and calcined for 6 hours at 330° C.

Examples 1 and 2 differ only in that the palladium nitrate solution in Example 1 was used for pre-swelling of the polymer. In Example 2, the aqueous palladium nitrate solution was mixed with pseudoboehmite and the polymer.

Analytical data of the catalyst according to Example 2:

Weight per liter [g/l]: 376

BET surface area [m²/g]: 276

Pore volume (DIN 66 132) [ml/g]: 1.09 determined by mercury porosimetry (J. v. Brakel et al., Powder Technology 29 (1991), 1)

Mean diameter of the macropores [nm]: 500

Mean diameter of the micro- and mesopores [nm]: 4.5

Proportion of macropores [% by volume]: 35

A comparison of electron micrographs of sections through the catalysts prepared according to Examples 1 and 2 shows that, in the novel catalyst, the active component is present for the most part (>80 %) in the macropores. In the comparative catalyst on the other hand, the active component is present predominantly in the micropores and only to an extent of about 10 % in the macropores.

Example 3

Use of the supported catalysts according to Examples 1 and 2 for the selective hydrogenation of a $C_4$ stream A $C_4$ stream according to the following table was reacted over the catalysts according to Examples 1 and 2 by the trickle-bed method at 50° C. and 14.1 bar at a space velocity of 6.4 l per l per h, based on the $C_4$ stream.

The catalysts were reduced before the hydrogenation in the stream of hydrogen (atmospheric pressure, 150° C., 8 h, 20 l of $H_2$ per l per h).

The table below shows the composition of the $C_4$ stream and the hydrogenation product:

| | Composition in mol % | | |
|---|---|---|---|
| | | Hydrogenation product | |
| | $C_4$ stream | Example 1 | Example 2 |
| Butadiene | 45.6 | 3.2 | 3.3 |

-continued

| | Composition in mol % | | |
|---|---|---|---|
| | | Hydrogenation product | |
| | C$_4$ stream | Example 1 | Example 2 |
| But-1-ene | 15.9 | 38.7 | 36.6 |
| Trans-but-2-ene | 4.9 | 20.2 | 20.1 |
| Cis-but-2-ene | 3.7 | 7.3 | 7.5 |
| Isobutene | 24.2 | 24.2 | 24.2 |
| Isobutane | 1.5 | 1.5 | 1.5 |
| n-Butane | 4.2 | 4.9 | 6.8 |

The novel catalyst hydrogenates butadiene clearly more selectively to butenes, which can be seen from the markedly lower formation of n-butane.

Over a conventional catalyst (0.3 % by weight of Pd on α-Al$_2$O$_3$, weight per liter 1100 g/l), a lower selectivity (n-butane formation about 1%) is obtained for the same butadiene conversion. The advantages of the novel catalyst, owing to its lower weight per liter, are furthermore a space velocity which is higher by a factor of 2.8 (based on the catalyst material) and a content of active component which is smaller by a factor of 2.8.

Example 4

Preparation of a Pd/Ag coated catalyst 3.72 g of an aqueous palladium nitrate solution (11% by weight of Pd) and 6.44 g of silver nitrate were dissolved in 150 ml of dilute ammonia. This Pd- and Ag-containing solution was added to 6 g of a high molecular weight sodium polyacrylate (90 % of the acid groups neutralized, crosslinked with 0.4 % of polyethylene glycol having a molecular weight of 1500) which can bind 300 times its own weight of water.

After 1 hour, the gel-like material was kneaded with 280 g of pseudoboehmite (surface area after calcination at 600° C.: 300 m$^2$/g). After the addition of a total of 175 ml of water, kneading was carried out for 1 hour. The material was extruded at a pressure of 60 bar to give 4.0 mm extrudates, which were dried for 16 hours at 120° C. and calcined for 4 hours at 400° C.

The calcined extrudates were milled in a ball mill. Steatite beads (diameter 4.3–4.7 mm) were coated with this material. The granulating liquid used was a 4.2 percent strength aluminum nitrate solution. The coated beads were dried for 16 hours at 90° C. and calcined for 3 hours at 530° C.

The prepared beads had a Pd content of 0.02 % by weight and an Ag content of 0.2 % by weight. This method gives a catalyst which carries the active components in a macroporous coat, the active components being concentrated in the macropores of the coat.

Example 5

Use of the catalyst described under Example 4 for the selective hydrogenation of acetylene in the C$_2$ stream The Pd/Ag coated catalyst described under Example 4 was used for the selective gas-phase hydrogenation of acetylene in the C$_2$ stream.

A reactor having a catalyst volume of 66 ml was fed with 200 l/h of a C$_2$ stream (composition 99 % by volume of ethylene, 1 % by volume of acetylene) and 2.2 l/h of hydrogen. At 20 bar and a reactor inlet temperature of 31° C., an acetylene conversion of 90 % and a selectivity of 78 % were obtained.

Example 6

Use of the novel catalyst according to Example 1 for the selective hydrogenation of methylacetylene and propadiene in a C$_3$ stream in the liquid phase A C$_3$ stream according to the following table was reacted over the novel catalyst according to Example 1 by the liquid phase method at an inlet temperature of 4° C. and 20 bar and a space velocity of 9.5 kg per 1 per h, based on the C$_3$ stream. The molar ratio of hydrogen to methylacetylene/propadiene was 1.1:1

The catalyst prepared according to Example 1 was reduced before the hydrogenation in the hydrogen stream (atmospheric pressure, 50° C., 3 h, 20 l of H$_2$ per 1 per h).

The methylacetylene/propadiene content was reduced from 4.07 % to <140 ppm.

| | Composition in mol % | |
|---|---|---|
| | C$_3$ stream | Hydrogenation product |
| Methylacetylene | 2.32 | <20 ppm |
| Propadiene | 1.75 | 120 ppm |
| Propene | 90.78 | 93.69 |
| Propane | 5.13 | 5.8 |
| Unknown compounds | 0.02 | 0.5 |

We claim:

1. A supported catalyst obtained by steps a to d in the given order:
   a) dissolving as a catalytically active component a salt of a transition metal or a sol of Pd, Pt, Ag or Cu or its intermediate in a water-miscible solvent,
   b) adding an organic polymer which is capable of binding at least ten times its own weight of water to the solution obtained in step a,
   c) mixing the polymer with a catalyst carrier,
   d) molding the material thus obtained, drying and calcining.

2. A supported catalyst as defined in claim 1, which is prepared using water or a mixture of water and ammonia as the solvent.

3. A supported catalyst as defined in claim 1, which is prepared using a crosslinked sodium polyacrylate as the organic polymer.

4. A supported catalyst as defined in claim 1, which is prepared using a water-soluble palladium salt as an intermediate for the active component.

5. A supported catalyst as defined in claim 1, wherein the catalytically active component is palladium acetate, palladium nitrate or palladium chloride; wherein the solvent is water or a mixture of water and ammonia and wherein the organic polymer is a crosslinked sodium polyacrylate.

* * * * *